United States Patent
Fujimoto et al.

(10) Patent No.: US 11,214,590 B2
(45) Date of Patent: Jan. 4, 2022

(54) PHOTORESPONSIVE NUCLEOTIDE ANALOG CAPABLE OF PHOTOCROSSLINKING IN VISIBLE LIGHT REGION

(71) Applicants: JAPAN ADVANCED INSTITUTE OF SCIENCE AND TECHNOLOGY, Nomi (JP); NICCA CHEMICAL CO., LTD., Fukui (JP)

(72) Inventors: Kenzo Fujimoto, Nomi (JP); Shigetaka Nakamura, Nomi (JP)

(73) Assignees: JAPAN ADVANCED INSTITUTE OF SCIENCE AND TECHNOLOGY, Ishikawa (JP); NICCA CHEMICAL CO., LTD., Fukui (JP)

( * ) Notice: Subject to any disclaimer, the term of this patent is extended or adjusted under 35 U.S.C. 154(b) by 0 days.

(21) Appl. No.: 16/631,653

(22) PCT Filed: Jul. 25, 2018

(86) PCT No.: PCT/JP2018/027961
§ 371 (c)(1),
(2) Date: Jan. 16, 2020

(87) PCT Pub. No.: WO2019/022158
PCT Pub. Date: Jan. 31, 2019

(65) Prior Publication Data
US 2020/0172563 A1    Jun. 4, 2020

(30) Foreign Application Priority Data
Jul. 26, 2017   (JP) .............. JP2017-144897

(51) Int. Cl.
C07H 19/23   (2006.01)
C07H 21/04   (2006.01)

(52) U.S. Cl.
CPC ............ *C07H 19/23* (2013.01); *C07H 21/04* (2013.01)

(58) Field of Classification Search
None
See application file for complete search history.

(56) References Cited

U.S. PATENT DOCUMENTS

| | | | |
|---|---|---|---|
| 5,082,934 A | 1/1992 | Saba et al. | |
| 6,005,094 A | 12/1999 | Simon et al. | |
| 10,450,334 B2 * | 10/2019 | Fujimoto | B01J 19/123 |
| 2010/0274000 A1 | 10/2010 | Fujimoto et al. | |
| 2011/0034683 A1 | 2/2011 | Fujimoto et al. | |
| 2016/0031918 A1 | 2/2016 | Fujimoto et al. | |
| 2016/0326207 A1 | 11/2016 | Fujimoto et al. | |
| 2020/0172563 A1 | 6/2020 | Fujimoto et al. | |

FOREIGN PATENT DOCUMENTS

| | | |
|---|---|---|
| CN | 107163169 | 9/2017 |
| EP | 2 216 338 | 8/2010 |
| EP | 2 980 073 | 2/2016 |
| EP | 3660021 | 6/2020 |
| JP | 4-506206 A | 10/1992 |
| JP | 5-507419 | 10/1993 |
| JP | 2001-348398 A | 12/2001 |
| JP | 3753938 B2 | 3/2006 |
| JP | 3753942 B2 | 3/2006 |
| JP | 4814904 B2 | 11/2011 |
| JP | 4940311 B2 | 5/2012 |
| JP | 5925383 | 4/2016 |
| WO | 92/02532 | 2/1992 |
| WO | 2005/083073 | 9/2005 |
| WO | 2009/066447 A1 | 5/2009 |
| WO | 2010/147673 | 12/2010 |
| WO | 2014/157565 | 10/2014 |
| WO | 2019/022158 | 1/2019 |
| WO | 2020/158687 | 8/2020 |

OTHER PUBLICATIONS

International Search Report dated Aug. 28, 2018, issued in counterpart International Application No. PCT/JP2018/027961. (2 pages).
Vronteli et al., "Synthesis of fused pyranocarbazolones with biological interest", Arkivoc, (2015), No. 3, pp. 111-123. Cited in Specification. (13 pages).
Rodighiero et al., "Pyrrolocoumarin Derivatives as Potential Photoreagents Toward DNA", Journal of Heterocyclic Chemistry, (1987), vol. 24, pp. 1041-1043. Cited in Specification. (3 pages).
Koshimura et al., "Ultrafast Reversible Photo-Cross-Linking Reaction: Toward in Situ DNA Manipulation", Organic Letters, (2008), vol. 10, pp. 3227-3230. Cited in Specification. (4 pages).
Fujimoto et al., "DNA Photo-cross-linking Using Pyranocarbazole and Visible Light", Organic Letters, Apr. 27, 2018, vol. 20, pp. 2802-2805 Cited in Specification. (4 pages).
Nakamura et al., "Rapid Photopolymerization of Oligodeoxynucleotides by 3-Cyanovinylcarbazole mediated DNA Photocrosslinking", Journal of Photopolymer Science and Technology, (2014), vol. 27, No. 4, pp. 485-490. Cited in Specification. (6 pages).
Notification of Transmittal of Translation of the International Preliminary Report on Patentability (PCT/IPEA/Form 409) of International Application No. PCT/JP2018/027961 dated Jan. 30, 2020 (6 pages).

(Continued)

*Primary Examiner* — Traviss C McIntosh, III
(74) *Attorney, Agent, or Firm* — Wenderoth, Lind & Ponack, L.L.P.

(57) ABSTRACT

Provided are a compound represented by formula I that can be used in nucleic acid photoreaction techniques, and a photoreactive crosslinking agent comprising the compound.

(I)

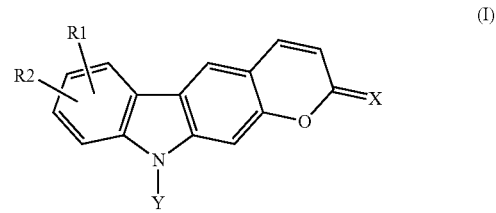

14 Claims, 11 Drawing Sheets

(56) References Cited

OTHER PUBLICATIONS

Extended (supplementary) European Search Report dated Oct. 31, 2016, issued in European Patent Application No. 14773781.1. (6 pages).
International Search Report dated Jun. 10, 2014, issued in Application No. PCT/JP2014/058988 (2 pages).
Notification of Transmittal of Translation of the International Preliminary Report on Patentability (Form PCT/IB338) issued in International Application No. PCT/JP2014/058988.(16 pages).
Fujimoto et al., "DNA photo-cross-linking using a pyranocarbazole-modified oligodeoxynynucleotide with a D-threoninol linker", The Royal Society of Chemistry, 2019, vol. 9, pp. 30693-30697.
Gupta et al., "Peptide nucleic acids: Advanced tools for biomedical applications", Journal of Biotechnology, 2017, vol. 259, pp. 148-159.
Haque et al., "Photoswitchable Formation of a DNA Interstrand Cross-Link by a Coumarin-Modified Nucleotide", Angew. Chem. Int. Ed., 2014, vol. 53, pp. 7001-7005
Kean et al., "Photochemical Cross-Linking of Psoralen-Derivatized Oligonucleoside Methylphosphonates to Rabbit Globin Messenger RNA", Biochemistry, 1988, vol. 27, pp. 9113-9121.
Lee et al., "Interaction of Psoralen-Derivatized Oligodeoxyribonucleoside Methylphosphonates with Single-Stranded DNA", Biochemistry, 1988, vol. 27, 3197-3203.
Sakamoto et al., "DNA Photo-Cross-Linking Using 3-Cyanovinylcarbazole Modified Oligonucleotide with Threoninol Linker", Organic Letters, 2015, vol. 17, No. 4, pp. 936-939.
Notification of Transmittal of Translation of the International Preliminary Report on Patentabililty (Form PCT/IB/338) issued in counterpart International Application No. PCT/JP2018/027169 dated Feb. 6, 2020 with Forms PCT/IB/373 and PCT/ISA/237. (5 pages).
Gia et al., "Pyrrolocoumarin Derivatives: DNA-Binding Properties", Journal of Photochemishy and Photobiology, B; Biology, 1988, vol. 2, pp. 435-442.
International Search Report dated Oct. 2, 2018, issued in counterpart International Application No. PCT/JP2018/027169 (2 pages).
Kashida et al., "Control of the Chirality and Helicity of Oligomers of Serinol Nucleic Acid (SNA) by Sequence Design" Agnew. Chem. Int. Ed. 2011, vol. 50, pp. 1285-1288 (2011).
Extended European Search Report dated Feb. 17, 2021 in corresponding European Patent Application No. 18837260.1.
Extended European Search Report dated Mar. 24, 2021 in corresponding European Patent Application No. 18838876.3.

* cited by examiner

[FIG. 1a]
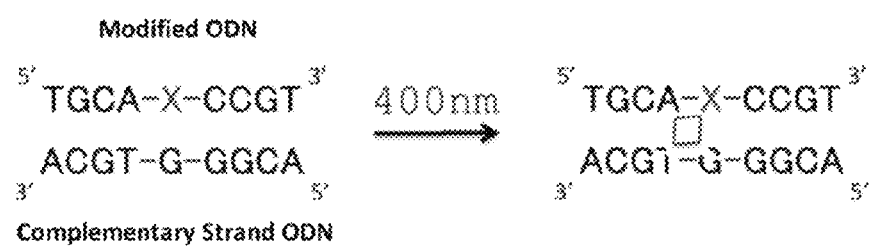

[FIG. 1b]
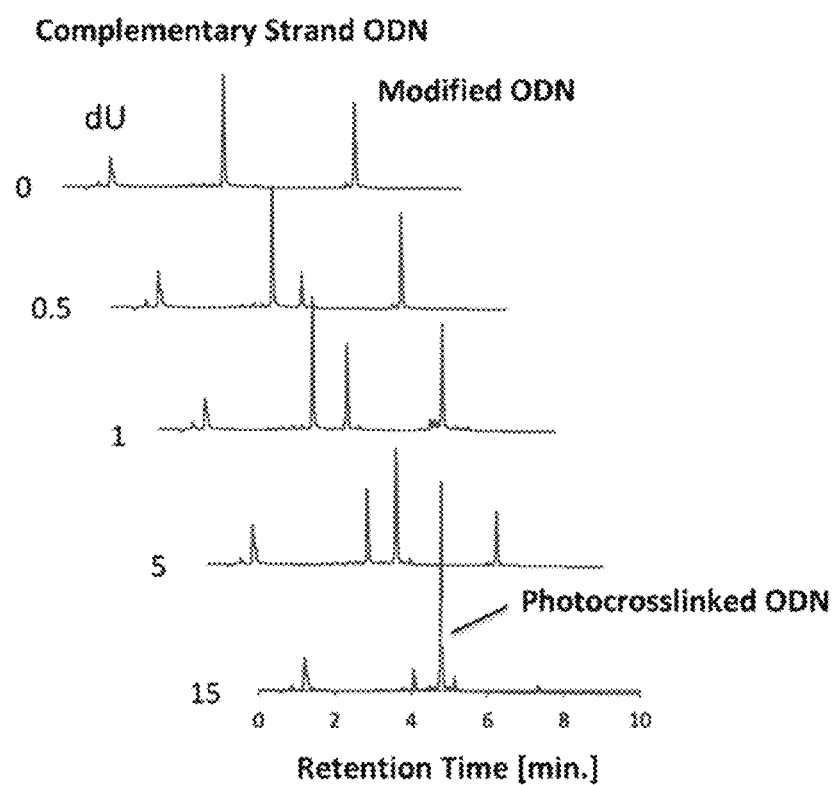

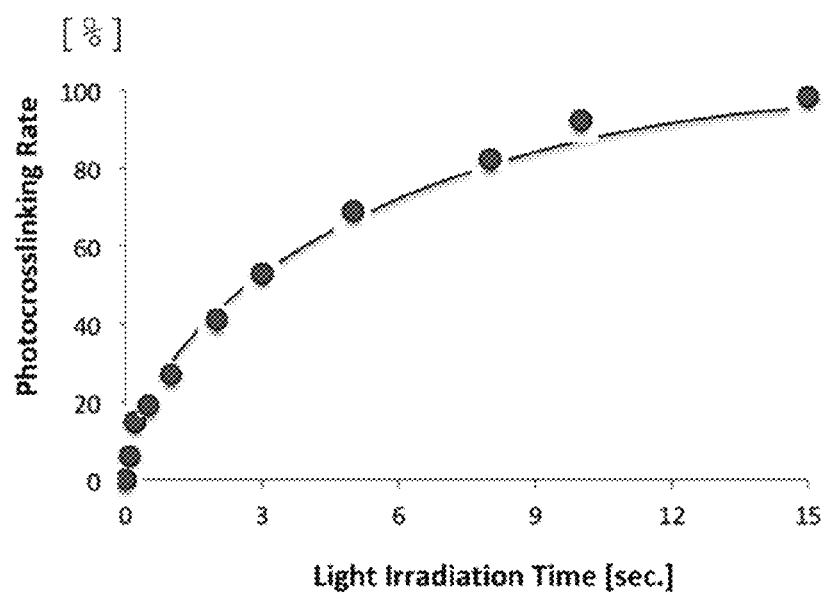
[FIG 1c]

[FIG. 2a]
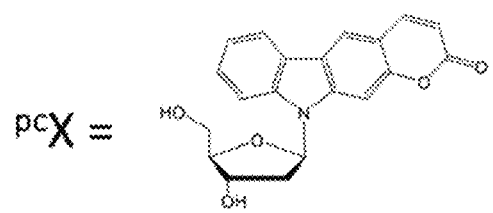
ODN (pcX)
5' TGCA pcX CCGT 3'
ACGT--GGGCA
3'         5'
    cODN
ODN (pcX)
5' TGCA pcX CCGT 3'
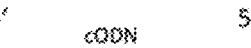
ACGT--GGGCA
3'         5'
    cODN

[FIG. 2b]
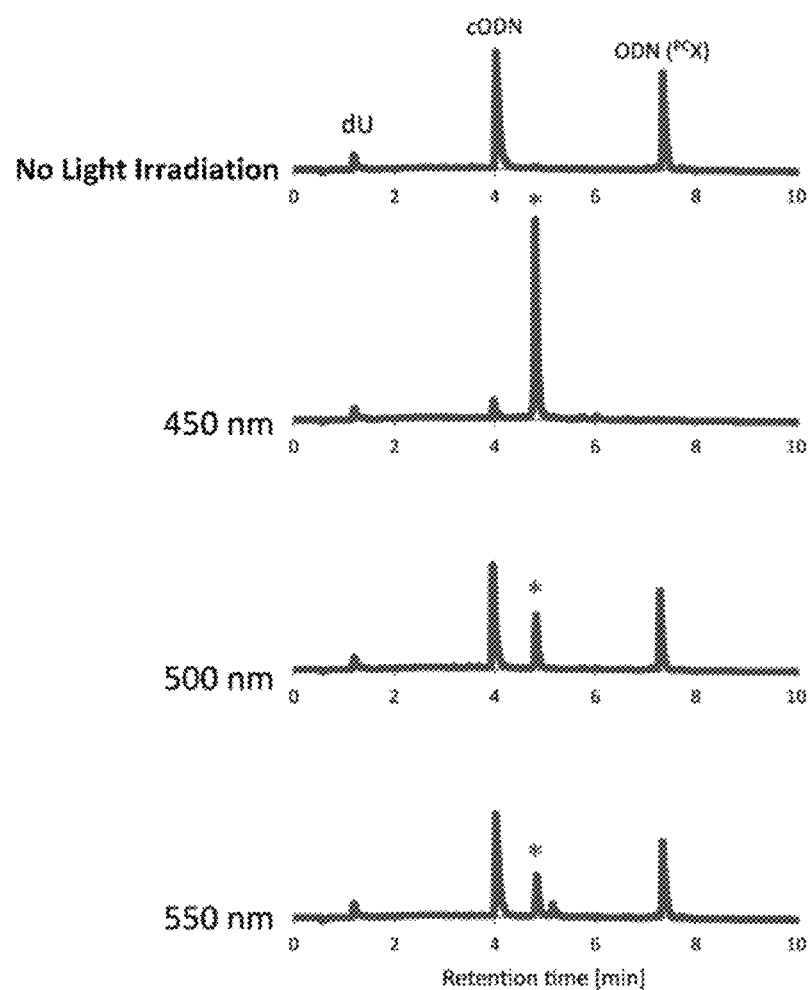

[FIG. 3a]
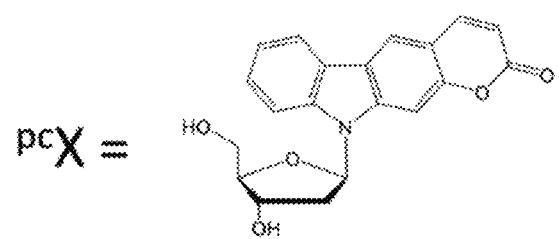
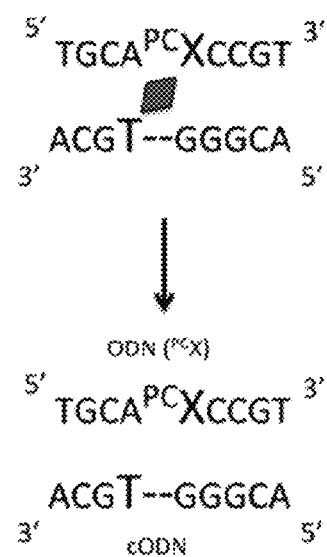

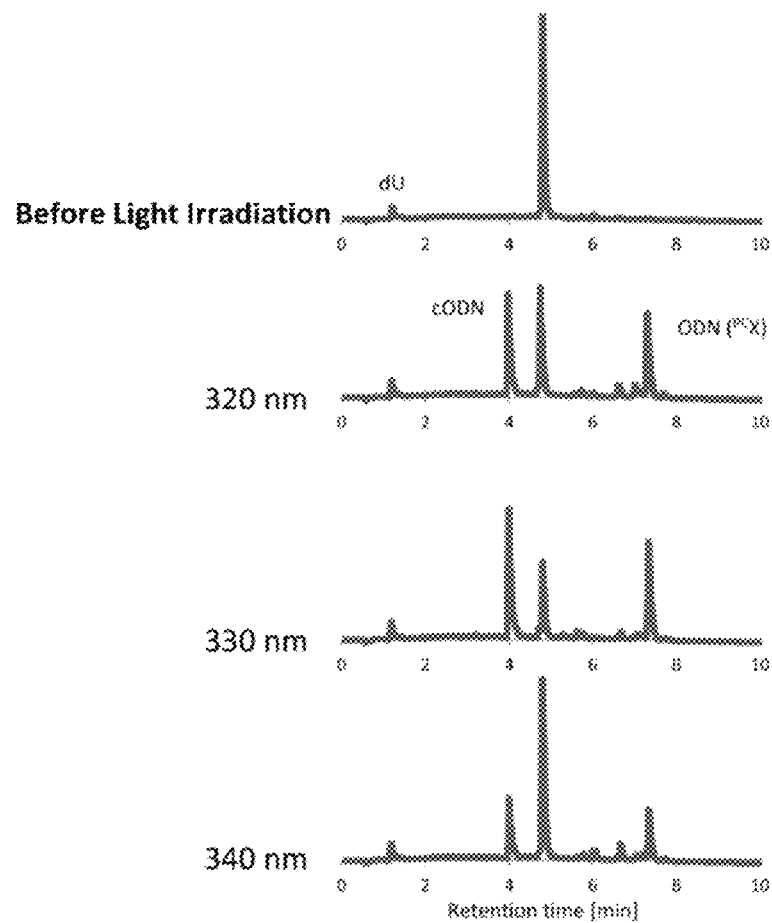
[FIG. 3b]

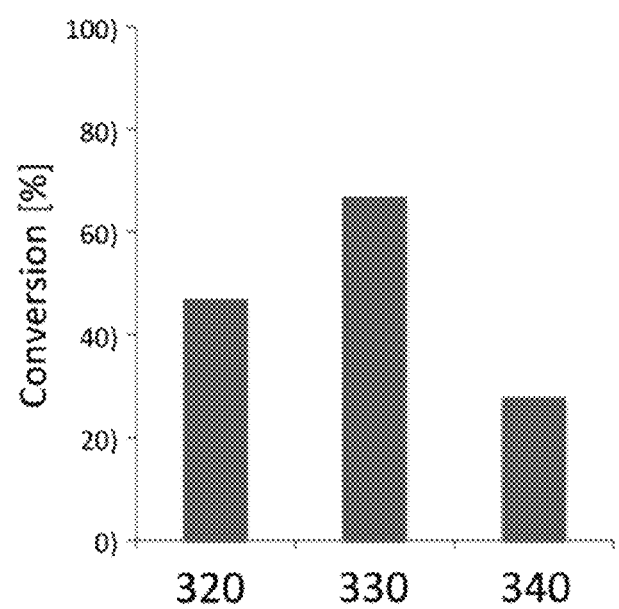
[FIG. 3c]

[FIG. 4]
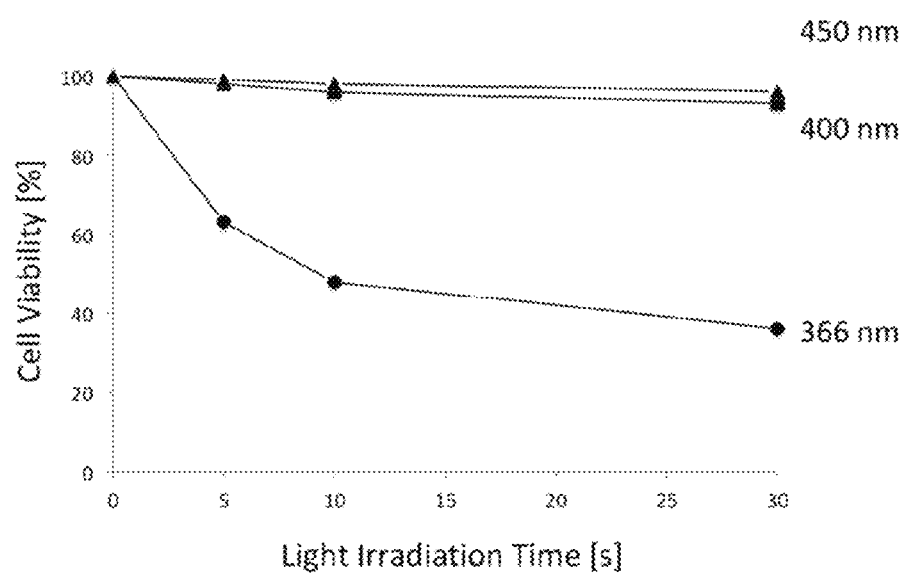

[FIG. 5]

5'-TGCAXCCGT-3'

3'-ACGTGGGCA-5'

450 nm ↓

5'-TGCAXCCGT-3'
3'-ACGTGGGCA-5'

[FIG. 6]
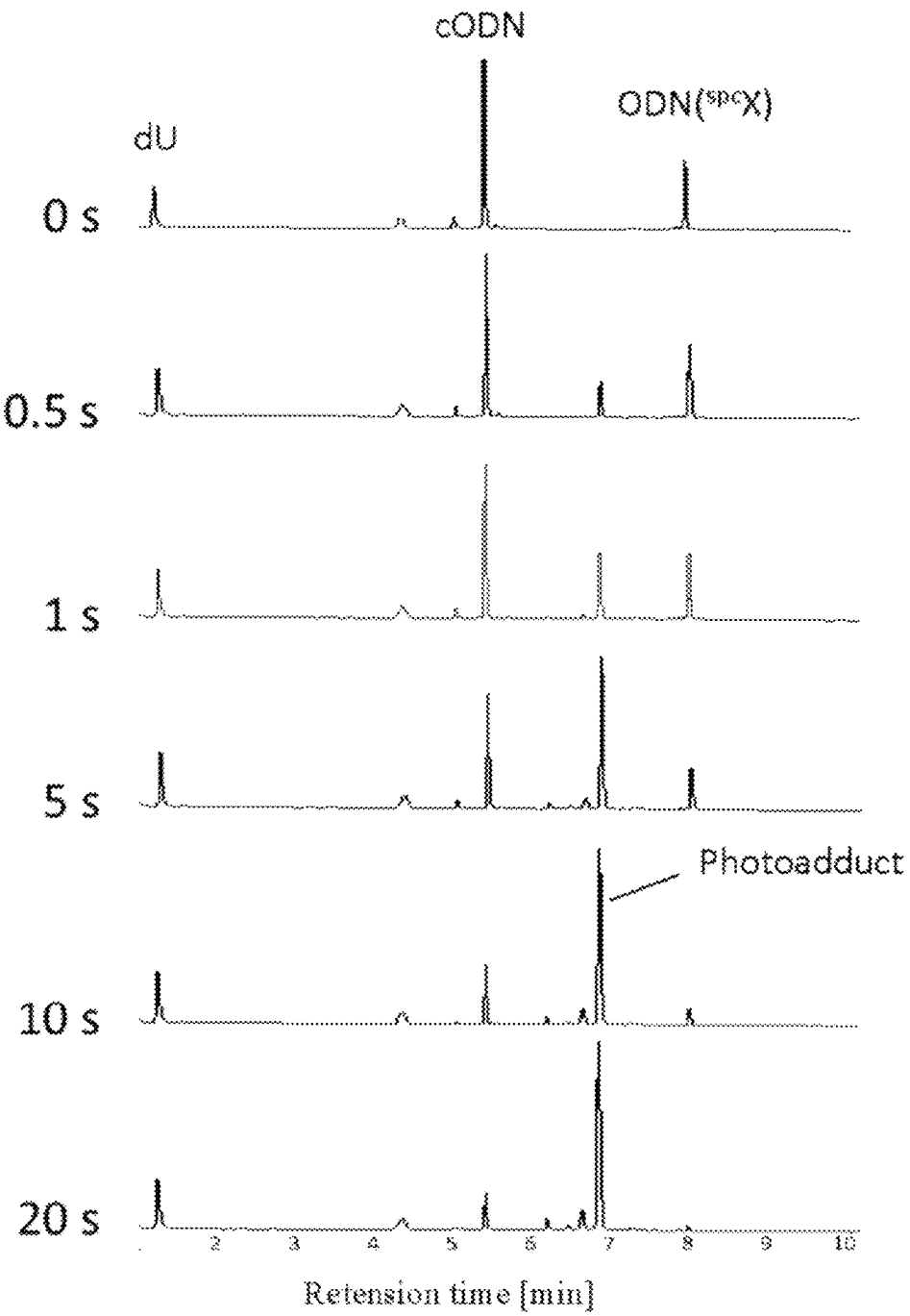

PHOTORESPONSIVE NUCLEOTIDE ANALOG CAPABLE OF PHOTOCROSSLINKING IN VISIBLE LIGHT REGION

TECHNICAL FIELD

The present invention relates to a photoresponsive nucleotide analog capable of photocrosslinking in visible light region.

BACKGROUND ART

Basic techniques in the field of molecular biology include ligation of nucleic acids and crosslinking of nucleic acids. The ligation and crosslinking of nucleic acids are used for introduction of genes or detection of nucleotide sequences, or inhibition of gene expressions, for example, in combination with hybridization. Therefore, the techniques of the ligation and crosslinking of nucleic acids are very important techniques that are used in basic molecular biology researches, as well as, for example, diagnosis or treatment in the medical field, or development or production of therapeutic agents and diagnostic agents, or development or production of enzymes, microorganisms or the like in the industrial and agricultural fields.

Known as photoreaction techniques of nucleic acids are photoligation techniques using 5-cyanovinyldeoxyuridine (Patent Document 1: Japanese Patent No. 3753938 B; Patent Document 2: Japanese Patent No. 3753942 B); and photocrosslinking techniques using modified nucleosides having a 3-vinylcarbazole structure at the base site (Patent Document 3: Japanese Patent No. 4814904 B; Patent Document 4: Japanese Patent No. 4940311 B).

Furthermore, it has recently become possible to construct various nanostructures using the ability of nucleic acids to form double strands, and the ligation and crosslinking techniques have become important in the field of nanotechnology. For example, Non-Patent Document 1 discloses a technique for providing heat resistance to a nano-sheet consisting of oligo DNAs by photocrosslinking of nucleic acids.

CITATION LIST

Patent Literatures

Patent Document 1: Japanese Patent No. 3753938 B
Patent Document 2: Japanese Patent No. 3753942 B
Patent Document 3: Japanese Patent No. 4814904 B
Patent Document 4: Japanese Patent No. 4940311 B

Non-Patent Literature

Non-Patent Document 1: J. Photopoly. S. Tech., 2014, 27, 485

SUMMARY OF INVENTION

Technical Problem

Because of the importance of the photoreaction technique of nucleic acids, there is a further need for novel compounds that can be used for the photoreaction technique of nucleic acids. An object of the present invention is to provide a novel photoreactive compound that can be used for a photoreaction technique of nucleic acids, and a photoreactive crosslinking agent using the photoreactive compound.

Solution to Problem

As a result of intensive studies for photoreactive compound that will be photoreactive crosslinking agent capable of being used for the photoreaction technique of nucleic acids, the present inventors have found that a compound having a pyranocarbazole skeleton structure in place of a base moiety of a nucleic acid will be such a photoreactive crosslinking agent capable of being used for the photoreaction technique of nucleic acids, and have arrived at the present invention.

The compound according to the present invention has a characteristic pyranocarbazole structure and exhibits a photocrosslinking property due to such a relatively small structure. Therefore, the compound according to the present invention can be variously modified and used in various applications. Furthermore, the characteristic structure of the compound according to the present invention is similar to a base of nucleic acid. Therefore, the compound according to the present invention can be used as an artificial base (artificial nucleic acid base). That is, the characteristic structure of the compound according to the present invention can be introduced as an artificial base to produce an artificial nucleoside (a nucleoside analog) and an artificial nucleotide (a nucleotide analog), and also an artificial nucleic acid (a modified nucleic acid) containing such an artificial nucleotide. When such an artificial nucleic acid forms a crosslink by photoreaction, it will form a photocrosslink formed from one strand to other strand of a double helix. Therefore, the photoreactive nucleic acids can be used as double helix photo-crosslinkers capable of reaction that is specific to a desired sequence.

A photoreactive crosslinking agent according to the present invention has a feature capable of being photocrosslinked by irradiation with light having a wavelength longer than that of the conventional one, for example, irradiation with light in the visible light region, which feature is derived from the characteristic pyranocarbazole structure. Therefore, when it is desired to avoid any damage to DNAs and cells as much as possible, the photoreactive crosslinking agent according to the present invention is particularly advantageous because it can be photocrosslinked by irradiation with light having a long wavelength.

It should be noted that the photoreactive compound according to the present invention initiates a photoreaction by light irradiation, but the term "photoreactive" may be referred to as "photoresponsive" for emphasizing the meaning that a compound which has previously been stable initiates reaction in response to a signal of the light irradiation.

Therefore, the present invention includes the following aspects (1) to (8):

(1)

A compound represented by the following formula I:

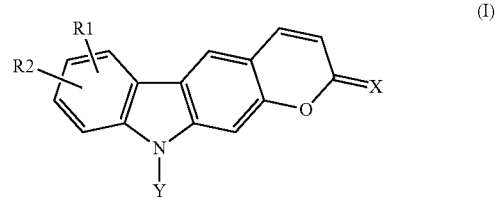

(I)

in which formula I:
X is an oxygen atom or a sulfur atom,
R1 and R2 are each independently a group selected from the group consisting of a hydrogen atom, a halogen atom, a —OH group, an amino group, a nitro group, a methyl group, a methyl fluoride group, an ethyl group, an ethyl fluoride group, and a C3 alkylsulfanyl group;
Y represents a hydrogen atom; a saccharide including ribose and deoxyribose; a polysaccharide including a polyribose chain and a polydeoxyribose chain of a nucleic acid; a polyether; a polyol; a polypeptide chain including a polypeptide chain of a peptide nucleic acid; or a water-soluble synthetic polymer.

(2) The compound according to (1), wherein Y is a group represented by the following formula II:

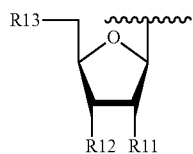

(II)

in which formula II,
R11 is a hydrogen atom or a hydroxyl group,
R12 is a hydroxyl group or a —O-$Q_1$ group,
R13 is a hydroxyl group or an —O-$Q_2$ group,
$Q_1$ is a group selected from the group consisting of:
a phosphate group formed together with O bonded to $Q_1$;
a nucleotide, nucleic acid or peptide nucleic acid linked via a phosphodiester bond formed by a phosphate group formed together with O bonded to $Q_1$; and
a protecting group selected from:
a trityl group, a monomethoxytrityl group, a dimethoxytrityl group, a trimethoxytrityl group, a trimethylsilyl group, a triethylsilyl group, a t-butyldimethylsilyl group, an acetyl group, and a benzoyl group;
$Q_2$ is a group selected from the group consisting of:
a phosphate group formed together with O bonded to $Q_2$;
a nucleotide, nucleic acid or peptide nucleic acid linked via a phosphodiester bond formed by a phosphate group formed together with O bonded to $Q_2$; and
a protecting group selected from:
a 2-cyanoethyl-N,N-dialkyl(C1-C4)phosphoramidite group, a methylphosphonamidite group, an ethylphosphonamidite group, an oxazaphospholidine group, a thiophosphite group, a TEA salt of —PH(=O)OH, a DBU salt of —PH(=O)OH, a TEA salt of —PH(=S)OH, and a DBU salt of —PH(=S)OH.

(3) The compound according to (1), wherein Y is a hydrogen atom, a group represented by the following formula Ill, or a group represented by the formula IV:

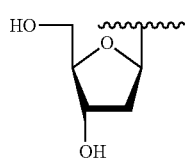

(III)

or

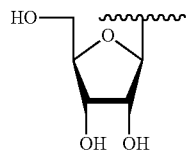

(IV)

(4) The compound according to (1), wherein the compound is a nucleoside having, as a base moiety, a group represented by the following formula Ib:

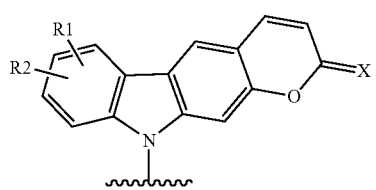

(Ib)

in which formula Ib,
X is an oxygen atom or a sulfur atom,
R1 and R2 are each independently a group selected from the group consisting of a hydrogen atom, a halogen atom, a —OH group, an amino group, a nitro group, a methyl group, a methyl fluoride group, an ethyl group, an ethyl fluoride group, and a C1-C3 alkylsulfanyl group.

(5) The compound according to (1), wherein the compound is a nucleotide having, as a base moiety, a group represented by the following formula Ib:

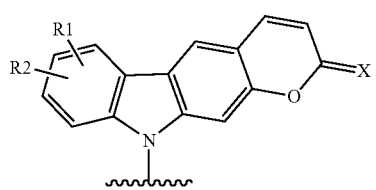

(Ib)

in which formula Ib,
X is an oxygen atom or a sulfur atom,
R1 and R2 are each independently a group selected from the group consisting of a hydrogen atom, a halogen atom, a —OH group, an amino group, a nitro group, a methyl group, a methyl fluoride group, an ethyl group, an ethyl fluoride group, and a C1-C3 alkylsulfanyl group.

(6) The compound according to (1), wherein the compound is a nucleic acid or a peptide nucleic acid having, as a base moiety, a group represented by the following formula Ib:

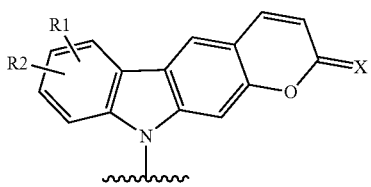

(Ib)

in which formula Ib,
X is an oxygen atom or a sulfur atom,
R1 and R2 are each independently a group selected from the group consisting of a hydrogen atom, a halogen atom, a —OH group, an amino group, a nitro group, a methyl group, a methyl fluoride group, an ethyl group, an ethyl fluoride group, and a C1-C3 alkylsulfanyl group.

(7)
A photoreactive crosslinking agent comprising the compound according to any one of (1) to (6).

(8)
A method for forming a photocrosslink between nucleic acid bases each having a pyrimidine ring, using the compound according to any one of (1) to (6).

Advantageous Effects of Invention

The present invention provides a novel compound that will be a photoreactive crosslinking agent capable of being used for a photoreaction technique of nucleic acids. This is due to a novel chemical structure having no natural base structure. According to the compound of the present invention, a photocrosslink can be formed by irradiation with light having a longer wavelength than the conventional photoreactive crosslinking agent, so that an inverse effect of irradiation with light on nucleic acids and cells can be minimized.

BRIEF DESCRIPTION OF DRAWINGS

FIG. 1a is an explanatory diagram showing a flow of photocrosslinking reaction.
FIG. 1b is a chart for UPLC analysis when a light irradiation time is changed from 0 to 15 seconds.
FIG. 1c is a graph created by calculating a photocrosslinking rate at each light irradiation time when the light irradiation time is changed from 0 to 15 seconds.
FIG. 2a is an explanatory diagram showing a flow of photocrosslinking reaction.
FIG. 2b is a chart for UPLC analysis when an irradiation light wavelength is changed from 450 to 550 nm.
FIG. 3a is an explanatory diagram showing a flow of photocleavage reaction.
FIG. 3b is a chart for UPLC analysis when an irradiating light wavelength is changed from 320 to 340 nm.
FIG. 3c is a graph showing a ratio (a conversion rate %) of photocrosslinked products cleaved by irradiation with light having each wavelength.
FIG. 4 is a graph comparing light irradiation time (seconds) with cell viability (%) at each wavelength.
FIG. 5 is an explanatory diagram showing a flow of photocrosslinking reaction by $^{SPC}X$.
FIG. 6 is a chart for UPLC analysis of a photocrosslinking test with $^{SPC}X$

DESCRIPTION OF THE PREFERRED EMBODIMENTS

The present invention will be described below in detail by providing specific embodiments. The present invention is not limited to the following specific embodiments as mentioned below.

[Structure of Compound]

A compound of the present invention includes a compound represented by the formula I:

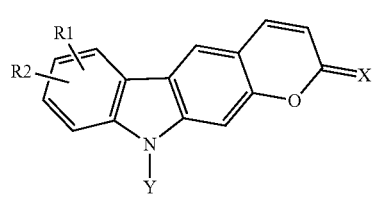

(I)

In the formula I, X is an oxygen atom or a sulfur atom.
In the formula I, R1 and R2 are each independently a group selected from the group consisting of a hydrogen atom, a halogen atom, a —OH group, an amino group, a nitro group, a methyl group, a methyl fluoride group, an ethyl group, an ethyl fluoride group, and a C1-C3 alkylsulfanyl group. Examples of the halogen atom include Br, Cl, F, and I atoms. Examples of the methyl fluoride group include —CH$_2$F, —CHF$_2$, and —CF$_3$. Examples of the ethyl fluoride group include —CH$_2$—CH$_2$F, —CH$_2$—CHF$_2$, —CH$_2$—CF$_3$, —CHF—CH$_3$, —CHF—CH$_2$F, —CHF—CHF$_2$, —CHF—CF$_3$, —CF$_2$—CH$_3$, —CF$_2$—CH$_2$F, —CF$_2$—CHF$_2$, and —CF$_2$—CF$_3$. Examples of the C1-C3 alkylsulfanyl group include —CH$_2$—SH, —CH$_2$—CH$_2$—SH, —CH(SH)—CH$_3$, —CH$_2$—CH$_2$—CH$_2$—SH, —CH$_2$—CH(SH)—CH$_3$ and —CH(SH)—CH$_2$—CH$_3$ groups. In a preferred embodiment, R1 and R2 can each independently be a hydrogen atom, a halogen atom, a —NH$_2$ group, a —OH group, a —CH$_3$ group, and preferably a hydrogen atom.

In a preferred embodiment, R1 can be a hydrogen atom while at the same time R2 can be a group as defined above.

In a preferred embodiment, when in the 6-membered ring at the left end in the formula I, the carbon atom to which the nitrogen atom is linked is numbered as a C1 position, and the carbon atoms of the 6-membered ring are sequentially numbered as C2, C3, C4, C5, and C6 positions clockwise, R1 and R2 can each independently be a substituent for the carbon atom at any position of C2, C3, C4, and C5 positions. In a preferred embodiment, R1 and R2 can be substituents at the C3 and C4 positions, respectively. In a preferred embodiment, R1 can be a substituent at the C3 position and R2 can be a hydrogen atom at the C4 position.

In the formula I, Y can be a hydrogen atom; a saccharide including ribose and deoxyribose; a polysaccharide including a polyribose chain and a polydeoxyribose chain of a nucleic acid; a polyether; a polyol; a polypeptide chain including a polypeptide chain of a peptide nucleic acid; or a water-soluble synthetic polymer.

In a preferred embodiment, the compound of the formula I can be a compound represented by the following formula I':

(Formula I')

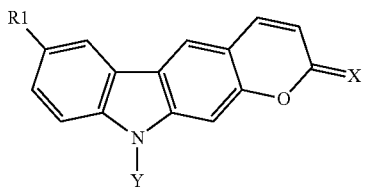
(I')

In the formula I', X is the group as defined in the formula I, R1 is the group as defined in the formula I, and Y is the group as define in the formula I.

In a preferred embodiment, the compound of formula I can be a compound represented by the following formula I":

(Formula I")

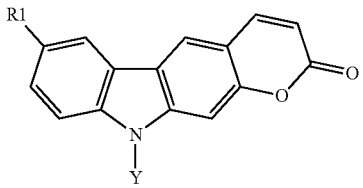
(I")

In the formula I", R1 is the group as defined in the formula I, and Y is the group as defined in the formula I.

In a preferred embodiment, the compound of the formula I can be a compound represented by the following formula I'":

(Formula I'")

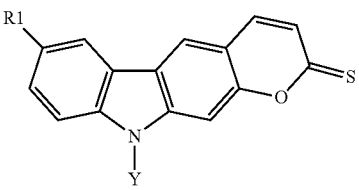
(I'")

In the formula I'", R1 is the group as defined in the formula I, and Y is the group as defined in the formula I.

In a preferred embodiment, Y can be a hydrogen atom, and in this case, the compound of the formula I is a compound represented by the following formula VI:

(VI)

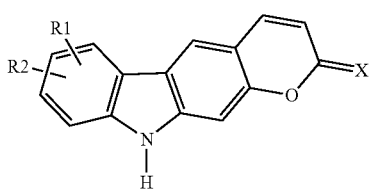
(VI)

In the formula VI, X is the group as defined in the formula I, and R1 and R2 are the groups as defined in the formula I and are located at the positions as defined in the formula I.

In a preferred embodiment, Y can be a hydrogen atom, and in this case, the compound of the formula I' is a compound represented by the following formula VI':

(VI')

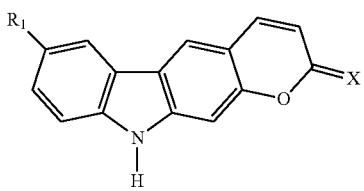
(VI')

In the formula VI', X is the group as defined in the formula I, and R1 is the group as defined in the formula I.

In a preferred embodiment, Y can be a group represented by the following formula II, and in this case, the compound of the formula I will be a compound represented by the following formula V:

(II)

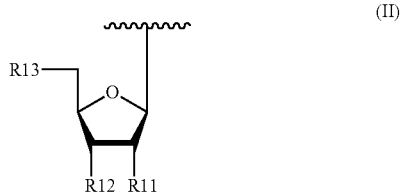
(II)

(V)

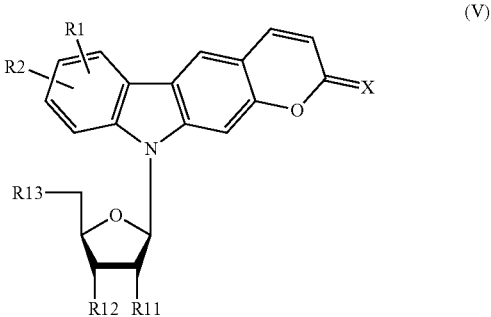
(V)

In the formula V, X is the group as defined in the formula I, R1 and R2 are the groups as defined in the formula I and are located at the positions as defined in Formula I, and R11, R12, and R13 are the groups as defined for the formula II.

In a preferred embodiment, Y can be the group represented by the above formula II, and in this case, the compound of the formula I' will be a compound represented by the following formula V':

(V')

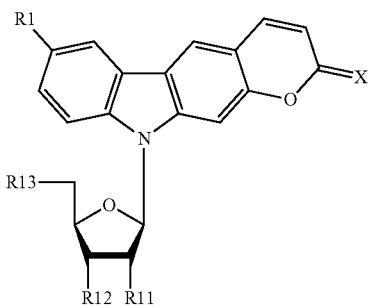

In the formula V', X is the group as defined in the formula I, R1 is the group as defined in the formula I, and R11, R12, and R13 are the groups as defined in the formula II.

In the formula II, R11 is a hydrogen atom or a hydroxyl group, R12 is a hydroxyl group or a —O-$Q_1$ group, and R13 is a hydroxyl group or a —O-$Q_2$ group.

The above $Q_1$ can be a group selected from the group consisting of:
a phosphate group formed together with O bonded to $Q_1$;
a nucleotide, nucleic acid or peptide nucleic acid linked via a phosphodiester bond formed by a phosphate group formed together with O bonded to $Q_1$; and
a protecting group selected from:
a trityl group, a monomethoxytrityl group, a dimethoxytrityl group, a trimethoxytrityl group, a trimethylsilyl group, a triethylsilyl group, a t-butyldimethylsilyl group, an acetyl group, and benzoyl group.

The above $Q_2$ can be a group selected from the group consisting of:
a phosphate group formed together with O bonded to $Q_2$;
a nucleotide, nucleic acid or peptide nucleic acid linked via a phosphodiester bond formed by a phosphate group formed together with O bonded to $Q_2$; and
a protecting group selected from:
a 2-cyanoethyl-N,N-dialkyl(C1-C4)phosphoramidite group, a methylphosphonamidite group, an ethylphosphonamidite group, an oxazaphospholidine group, a thiophosphite group, a TEA salt of —PH(=O)OH, a DBU salt of —PH(=O)OH, a TEA salt of —PH(=S)OH, and a DBU salt of PH(=S)OH.

The 2-cyanoethyl-N,N-dialkyl(C1-C4)phosphoramidite group has the following structure:

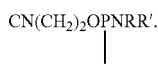

Each of the groups R and R' forming the dialkyl group as described above can be a C1-C4 alkyl group. Examples of such a 2-cyanoethyl-N,N-dialkyl(C1-C4)phosphoramidite group include a 2-cyanoethyl-N,N-dimethylphosphoramidite group, a 2-cyanoethyl-N,N-diethylphosphoroamidite group and a 2-cyanoethyl-N,N-diisopropylphosphoramidite group.

The methylphosphonamidite group has the following structure:

Each of the groups R and R' as described above can be a hydrogen atom or a C1-C4 alkyl group.

The ethylphosphonamidite group has the following structure:

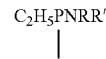

Each of the groups R and R' can be a hydrogen atom or a C1-C4 alkyl group.

The oxazaphospholidine group has the following structure:

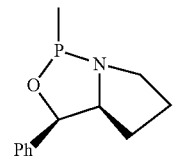

and also includes a substituted body in which the hydrogen atom is substituted by a C1 to C4 alkyl group, in the above structure.

The thiophosphite group has the following structure:

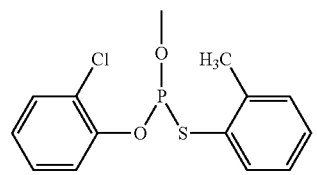 [SMILES: COP(Oc1ccccc1Cl)Sc1ccccc1C]

and also includes a substituted body in which the hydrogen atom is substituted by a C1 to C4 alkyl group, in the above structure.

Each of the TEA salt of —PH(=O)OH and the TEA salt of —PH(=S)OH is a triethylamine (TEA) salt of each.

Each of the DBU salt of —PH(=O)OH and the DBU salt of —PH(=S)OH is a diazabicycloundecene (DBU) salt of each.

In a preferred embodiment, $Q_1$ can be a nucleotide or nucleic acid linked via a phosphodiester bond formed by a phosphate group formed together with O bonded to $Q_1$.

In a preferred embodiment, $Q_1$ can be the protecting group as described above, preferably a dimethoxytrityl group, a trityl group, a monomethoxytrityl group, a trimethoxytrityl group, and particularly preferably the dimethoxytrityl group.

In a preferred embodiment, $Q_2$ can be a nucleotide or nucleic acid linked via a phosphodiester bond formed by a phosphate group formed together with O bonded to $Q_2$.

In a preferred embodiment, $Q_2$ can be the protecting group as described above, preferably a 2-cyanoethyl-N,N-dialkyl(C1-C4)phosphoramidite group, an oxazaphospholidine group, and a thiophosphite group, and more particularly 2-cyanoethyl-N, N-diisopropylphosphoramidite group.

[Nucleoside Analog]

In a preferred embodiment, Y can be a deoxyribose, i.e., a group represented by the following formula III, and in this case, the compound of the formula I is a nucleoside (deoxyribonucleoside) analog represented by the following formula VII:

(III)

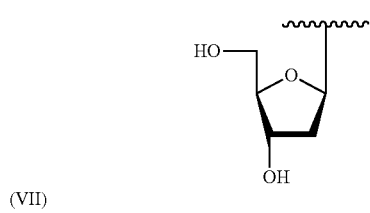

(VII)

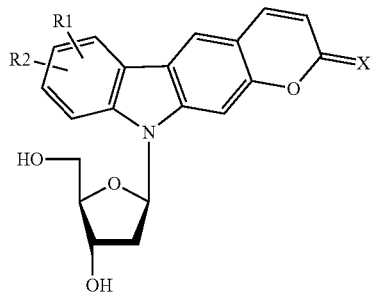

In the formula VII, X is the group as defined in the Formula I, and R1 and R2 are the groups as defined in the formula I and are located at the positions as defined in the formula I.

In a preferred embodiment, Y can be a deoxyribose, i.e., the group represented by the above formula III, and in this case, the compound of the formula I' is a nucleoside (deoxyribonucleoside) analog represented by the following formula VII':

(VII')

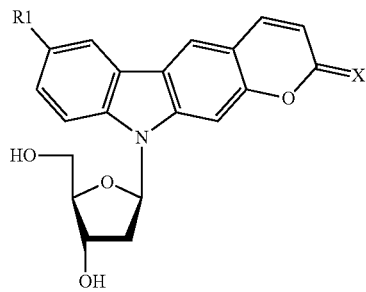

In the formula VII', X is the group as defined in the formula I, and R1 is the group as defined in the formula I.

In a preferred embodiment, Y can be a ribose, i.e., a group represented by the following Formula IV, and in this case, the compound of the formula I is a nucleoside (ribonucleoside) analog represented by the following formula VIII:

(IV)

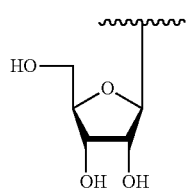

(VIII)

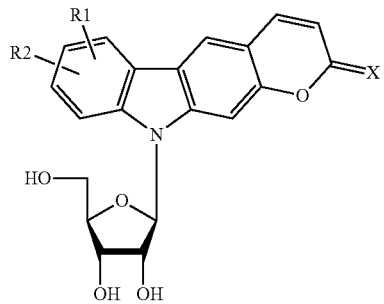

In the formula VIII, X is the group as defined in the formula I, and R1 and R2 are the group as defined in the formula I and are located at the positions as defined in the formula I.

In a preferred embodiment, Y can be a ribose, i.e., a group represented by the following Formula IV, and in this case, the compound of the formula I' is a nucleoside (ribonucleoside) analog represented by the following formula VIII':

(VIII')

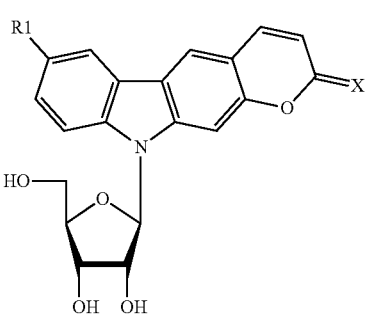

In the formula VIII', X is the group as defined in the formula I, and R1 is the group as defined in the formula I.

The nucleoside (ribonucleoside) analogs represented by the above formulae VII and VIII can refer to nucleosides (nucleoside analogs) each having a group represented by the following formula Ib, as a base moiety:

(Ib)

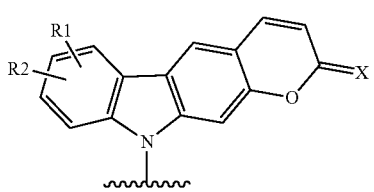

In the formula Ib, X is the group as defined in the formula I, and R1 and R2 are the groups as defined in the formula I and are located at the positions as defined in the formula I.

The nucleoside (ribonucleoside) analogs represented by the above formulas VII' and VIII' can refer to nucleosides (nucleoside analogs) each having a group represented by the following formula Ib', as a base moiety:

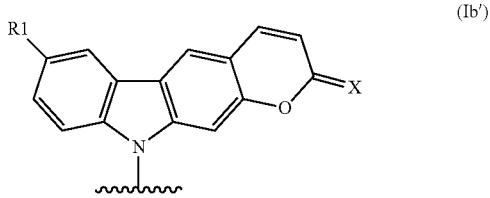

(Ib')

In the formula Ib', X is the group as defined in the formula I, and R1 is the group as defined in the formula I.

Further, the present invention also relates to a nucleotide (nucleotide analog) having a group represented by the above formula Ib or formula Ib' as a base moiety. Furthermore, the present invention also relates to a nucleic acid (modified nucleic acid) or a peptide nucleic acid (modified peptide nucleic acid) having a group represented by the above formula Ib or Ib' as a base moiety.

[Nucleotide Analog]

In a preferred embodiment, $Q_1$ can be a phosphate group formed together with O bonded to $Q_1$, and $Q_2$ can be a hydrogen atom. That is, the compound represented by the above formula I can be a photoresponsive artificial nucleotide analog molecule having the characteristic structure.

[Modified Nucleic Acid]

In a preferred embodiment, $Q_1$ can be a nucleotide or nucleic acid linked via a phosphodiester bond formed by a phosphate group formed together with O bonded to $Q_1$, and $Q_2$ can be a nucleotide or nucleic acid linked via a phosphodiester bond formed by a phosphate group formed together with O bonded to $Q_2$. That is, the compound represented by the above formula I can be a modified nucleic acid or modified oligonucleotide in which a photoresponsive artificial nucleotide analog having a characteristic structure is incorporated into the sequence. As used herein, the photoresponsive modified nucleic acid and the photoresponsive modified oligonucleotide thus prepared may be collectively referred to as a photoresponsive modified nucleic acid. In the modified nucleic acid according to the present invention, the photoresponsive artificial nucleotide analog having the characteristic structure may be located at the terminal in the sequence. In this case, it will be a modified nucleotide or modified nucleic acid in which only a side of $Q_1$ or $Q_2$ is linked via a phosphodiester bond formed by a phosphate group formed together with O bonded to $Q_1$ or $Q_2$. Alternatively, a peptide nucleic acid can be used in place of the nucleic acid as described above to provide a photoresponsive modified peptide nucleic acid in which the photoresponsive artificial nucleotide analog having the characteristic structure is incorporated into the sequence.

[Structure of Compound]

The compound according to the present invention does not have a base structure of purine bases or pyrimidine bases that should be possessed by a natural nucleoside and nucleotide, in the formula I or the like. Nevertheless, when the compound according to the present invention is formed as a single-stranded modified nucleic acid, it can form a double helix with a complementary single-stranded nucleic acid. A pyranocarbazole moiety can then form a crosslink by photoreaction.

[Reagent for Producing Modified Nucleic Acid]

In a preferred embodiment, $Q_1$ can be the protecting group as defined above, and $Q_2$ can be a phosphate group formed together with O bonded to $Q_2$, or a nucleotide or nucleic acid linked via a phosphodiester bond formed by a phosphate group formed together with O bonded to $Q_2$, or the protecting group as defined above. That is, the compounds represented by the above formulae I, I" and I''' can be producing reagents (synthetic reagents) for the photoreactive modified nucleic acid.

In a preferred embodiment, $Q_1$ can be the protecting group as defined above, and $Q_2$ can be a phosphate group formed together with O bonded to $Q_2$, or the protecting group as defined above. As is well known, the compound having such a structure can be used as a monomer for nucleic acid synthesis, and can be used as a reagent that can be employed by a known DNA synthesizer, for example, a reagent for synthesizing modified nucleic acids (a monomer for synthesizing modified nucleic acids), which can be employed by a phosphoramidite method and an H-phosphonate method.

Further, the structure in which $Q_1$ is the protecting group as defined above and $Q_2$ is a nucleotide or nucleic acid linked via a phosphodiester bond formed by a phosphate group formed together with O bonded to $Q_2$ can be a modified nucleic acid, rather than a so-called monomer. In such a case, it can be used as a producing reagent (synthesizing reagent) for extending the chain length.

Examples of the reagent for producing photoreactive modified nucleic acids (the reagent for synthesizing photoreactive modified nucleic acids) include monomers described as Compound 5 and Compound 6 in Scheme 1 as described below, and a monomer described in Scheme 2 as described below.

[Photoreactive Crosslinking Agent]

In the compound according to the present invention, the pyranocarbazole moiety can form a crosslink by photoreaction. When the compound according to the present invention is formed as a single-stranded modified nucleic acid, it can form a double helix with a complementary single-stranded nucleic acid, and the pyranocarbazole moiety can form a crosslink by photoreaction, so that a photocrosslink can be formed between the strands formed from one strand of the double helix to the other strand. That is, the compound according to the present invention can be used as a photoreactive crosslinking agent.

[Formation of Photocrosslink]

When the modified nucleic acid according to the present invention is used as a single-stranded nucleic acid, it can hybridize with a complementary single-stranded nucleic acid to form a double helix. In the formation of the double helix, the nucleic acid bases at positions where base pairs should be formed in the complementary strand with the pyranocarbazole structure portion can be freely selected without any particular limitation. When the formed double helix is irradiated with light, a crosslink can be formed by a photoreaction between the nucleic acid strands forming the double helix. The photocrosslink is formed between a nucleic acid base and the pyranocarbazole structural, the nucleic acid base being located at a position where a base pair is formed in the complementary strand, with a nucleic acid base located on the 5' terminal side by one base in the sequence from a position where the pyranocarbazole structural moiety is located as a nucleic acid base. In other words, the photocrosslink is formed between a nucleic acid base and the pyranocarbazole structure, the nucleic acid base being located at the 3' terminal side by one base in the sequence from a nucleic acid base at a position where a base pair should be formed with the pyranocarbazole structure moiety in the complementary strand moiety.

[Base Specificity of Photocrosslinking]

In the present invention, the counterpart base with which the pyranocarbazole structure can form a photocrosslink is a base having a pyrimidine ring. On the other hand, the pyranocarbazole structure does not form a photocrosslink with a base having a purine ring. In other words, the photocrosslinkable compound according to the present invention has specificity that it forms photocrosslinks with cytosine, uracil, and thymine as natural nucleic acid bases, whereas it does not form photocrosslinks with guanine and adenine.

[Sequence Selectivity of Photoreactive Crosslinking Agent]

The photoreactive modified nucleic acid (photocrosslinkable modified nucleic acid) according to the present invention can be photocrosslinked after hybridizing with a sequence having a base sequence complementary to the modified nucleic acid to form a double helix. This can allow photocrosslinking reaction to be performed only on the target specific sequence. In other words, the photoreactive crosslinking agent according to the present invention can impart very high base sequence selectivity by designing a sequence as needed.

[Wavelength of Light Irradiation]

A wavelength of light irradiated for photocrosslinking can be, for example, in a range of from 350 to 600 nm, and preferably in a range of from 400 to 600 nm, and more preferably in a range of from 400 to 550 nm, and even more preferably in a range of from 400 to 500 nm, and still more preferably in a range of from 400 to 450 nm. In particular, light containing a wavelength of 400 nm is preferable. In a preferred embodiment, single wavelength laser light in these wavelength ranges can be used. Thus, in the present invention, a photocrosslink can be formed by irradiation with light having a wavelength in the visible light region. The conventional photoreactive crosslinking agents require irradiation with light having a wavelength shorter than these ranges. According to the present invention, a photocrosslink can be formed by irradiation with light having a longer wavelength than the conventional photoreactive crosslinking agents, which is advantageous in that adverse effects on nucleic acids and cells due to light irradiation can be minimized.

[Cleavage of Photocrosslink]

According to the compound of the present invention, after forming the photocrosslink, photocleavage can be further carried out by irradiation with light. That is, the photoreactive compound according to the present invention enables reversible photocrosslinking, and can be used as a reversible photocrosslinking agent.

As recalled from the reversibility of the photocrosslinking, the use of the reversible photocrosslinking agent of the compound according to the present invention can allow the nucleic acid having a specific base sequence to be separated, recovered or detected under physiological conditions. Therefore, the present invention also relates to a method for separating, recovering, or detecting a nucleic acid having a desired base sequence using the reversible photocrosslinking agent.

The wavelength of light irradiated for photocleavage can be, for example, in a range of from 300 to 350 nm, and preferably in a range of from 300 to 340 nm. In particular, light containing a wavelength of 312 nm is preferable. In a preferred embodiment, single wavelength laser light in these wavelength ranges can be used.

[Photoreaction Temperature]

In a preferred embodiment, to proceed with the photocrosslinking reaction, irradiation with light is generally carried out at a temperature in a range from 0 to 50° C., and preferably from 0 to 40° C., and more preferably from 0 to 30° C., and even more preferably from 0 to 20° C., and still more preferably from 0 to 10° C., and still more preferably from 0 to 5° C. In order to proceed with the photocleavage reaction, irradiation with light is generally carried out at a temperature in a range from 55 to 100° C., and preferably from 60 to 100° C., and further preferably from 60 to 90° C., and more preferably from 60 to 80° C.

[Photoreaction Conditions]

Due to the use of photoreaction, the photocrosslinking and photocleavage according to the present invention have no particular restriction on a pH, a salt concentration or the like, and can be carried out by irradiation with light in a solution having a pH and a salt concentration where biopolymers such as nucleic acids can be stably present.

[Photoreaction Time]

The photocrosslinking and photocleavage according to the present invention proceed very rapidly. For example, in a case of psoralen known as a photoreactive compound, the photoreaction requires several hours (by irradiation with light having 350 nm), whereas, in the present invention, the photoreaction proceeds by irradiation with light having a much longer wavelength, for example, for only 10 seconds to 60 seconds (by irradiation with light having 400 nm) to causes photocrosslinking. That is, by using the photocrosslinking agent according to the present invention, the photoreaction can be allowed to proceed by irradiation with light, for example, for 1 to 120 seconds, or 1 to 60 seconds, to form a photocrosslink. Further, according to the photocrosslinking according to the present invention, the photoreaction can be allowed to proceed by irradiation with light, for example, for 1 to 120 seconds or 1 to 60 seconds, using the above wave length and temperature, to cleave the photocrosslink.

[Synthesis of Monomer for Synthesizing Modified Nucleic Acid and Modified Nucleic Acid]

A synthesizing monomer (producing reagent) for obtaining the modified nucleic acid according to the present invention (for example, compound 3, compound 4, compound 5, compound 6 in Scheme 1 as described below, or corresponding compounds in Scheme 2) can be obtained from a compound having a pyranocarbazole structure (for example, compound 2 in Scheme 1 as described below) using a method as shown in Scheme 1 or Scheme 2 as described below or a method known to one of ordinary skill in the art. The structure of the synthesizing monomer for the modified nucleic acid according to the present invention is as described above. The use of the monomer as a nucleic acid synthesizing reagent in a known method such as a phosphoramidite method and an H-phosphonate method can provide a nucleic acid or oligonucleotide in which the photoresponsive artificial nucleoside analog molecule (the compound of the formula VII or the formula VIII) is incorporated into the sequence (the modified nucleic acid according to the present invention) or a peptide nucleic acid. Thus, the synthesizing monomer for the modified nucleic acid according to the present invention is excellent in that it can be used as a nucleic acid synthesizing reagent in known techniques such as the phosphoramidite method and the H-phosphonate method.

EXAMPLES

Hereinafter, the present invention will be described in detail with reference to Examples. The present invention is not limited to Examples illustrated below.

[Synthesis of Nucleoside Analog (Photoreactive Element)]

A photoresponsive artificial nucleoside analog molecule (which may be referred to as a nucleoside analog or a photoreactive element or a photocrosslinking element) and a modified nucleic acid synthesizing monomer were synthesized along a synthetic route as shown in the following Scheme 1.

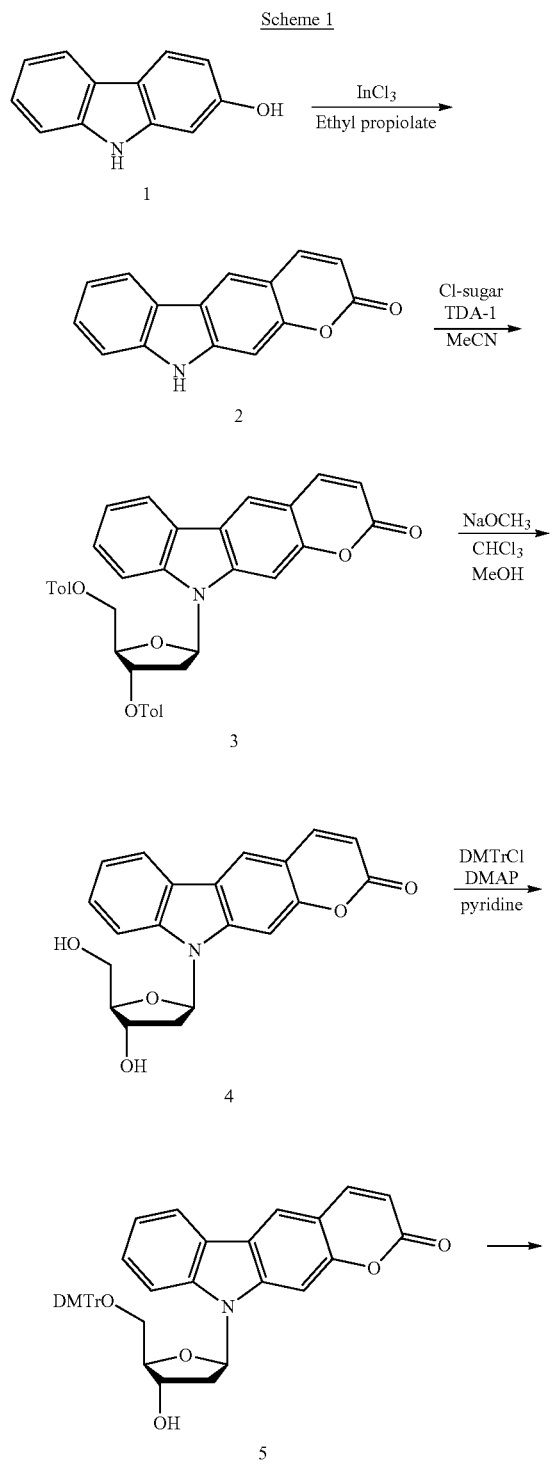

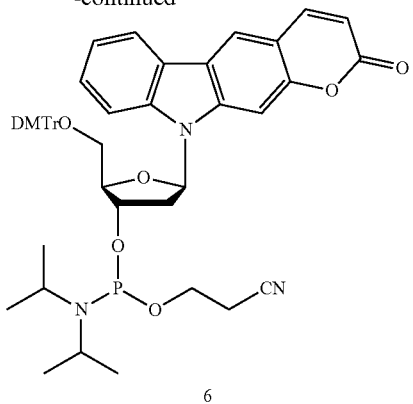

[Synthesis of Compound 2]

2-hydroxycarbazole (2.0 g, 11 mmol) and InCl$_3$ (260 mg, 1.18 mmol) were placed in a two-necked eggplant flask, a reflux tube was attached thereto, and the flask was purged with nitrogen. An oil bath was set at 90° C., and ethyl propiolate (4 ml) was added to the two-necked eggplant flask and stirred at 90° C. for 24 hours. After confirming the progress of the reaction by TLC, 2 mL of water was added to quench the reaction. It was dissolved in ethyl acetate and extracted. Dehydration was performed with sodium sulfate, and the solvent was removed by an evaporator. Purification was then performed by a column (hexane:ethyl acetate=8:1) to obtain Compound 2. (Yield: 503 mg, 2.75 mmol, Yield: 25%).

$^1$H-NMR (400 MHz, DMSO-d$_6$) δ11.67 (s, 1H), 8.47 (s, 1H), 8.17 (dt, 2H, J=11.4 Hz), 7.50-7.43 (m, 2H), 7.25 (dt, 1H, J=8.54 Hz), 6.33 (d, 1H, J=4.75 Hz)

[Synthesis of Compound 4]

Compound 2 (324 mg, 1.38 mmol) and KOH (224 mg, 4.00 mmol) were placed in a two-necked eggplant flask, and the flask was purged with nitrogen. 36 mL of dehydrated acetonitrile and 24 μL of TDA-1 were added and stirred for 30 minutes. Chlorosugar (674 mg, 1.94 mmol) was then added and the mixture was stirred overnight. After filtering the reaction solution, the solvent was removed by an evaporator. The mixed solution after the removal was dissolved in 40 mL of methanol, and 54 mg of sodium methoxide and 5 mL of chloroform were then added and stirred for 4 hours. Filtration and removal of the solvent were then performed by an evaporator. Purification was then performed using a column (chloroform) to obtain Compound 4 (Yield: 80 mg, 0.23 mmol, Yield: 17%).

$^1$H-NMR (400 MHz, DMSO-d$_6$) δ 8.50 (s, 1H), 8.18 (m, 2H), 7.50 (dd, 2H, J=8.28, 8.0), 7.31 (dt, 1H, J=7.17), 6.71 (dt, 1H, J=6.2), 6.38 (d, 1H, 4.6 Hz), 5.40 (d, 1H, J=5.4 Hz), 5.10 (dt, 1H, J=5.07 Hz), 3.95-3.87 (m, 3H), 2.74 (dt, 1H, J=14.0, 8.2 Hz), 2.26 (ddd, 1H, J=14.0, 6.9, 3.3 Hz)

[Synthesis of Compound 5 and Compound 6]

In the subsequent synthesis, dimethoxytritylation and amiditation were carried out according to a conventional method.

[Synthesis of Photoresponsive Nucleic Acid-Containing DNA]

A modified DNA was synthesized using an automatic DNA synthesizer (ABI 3400). The modified DNA was cut out with a 28% aqueous ammonia solution, and then heated at 65° C. for 4 hours to achieve de-protection. The ammonia was removed by SpeedVac and purified by HPLC. Analysis with MALDI-TOF-MS was then performed to identify a target product.

Calcd. for [M+H]$^+$ 2798.40, Found 2798.72.

[Photocrosslinking Reaction]

A 50 mM cacodylic acid buffer (pH 7.4) containing 10 µM of modified ODN, 10 µM of complementary ODN, 50 µM of deoxyuridine, and 100 mM of NaCl was heated at 90° C. for 1 minute and allowed to stand at 4° C. Irradiation with light having 400 nm was then performed at 4° C. using a UV-LED (OmniCure, LX405-S). FIG. 1a is an explanatory diagram showing the flow of the photocrosslinking reaction.

[UPLC Analysis]

50 µL of a DNA sample was transferred to a vial for UPLC, and UPLC (ultra-high performance liquid chromatography) analysis was performed. For analysis, 50 mM of ammonium formate and acetonitrile were used, and the solvent ratio was linearly changed such that ammonium formate was 100% at the start of the analysis, and ammonium formate was 90% and acetonitrile was 10% at the time of 10 minutes. The analysis was performed at a flow rate of 0.2 mL/min and at a detection wavelength of 260 nm. FIG. 1b and FIG. 1c summarize these results.

[Result]

FIG. 1b is a chart for UPLC analysis when a light irradiation time is changed from 0 to 15 seconds. The horizontal axis in FIG. 1b is a retention time [minutes]. The positions of the peaks of the complementary strand ODN, the modified ODN, and the photocrosslinked ODN are shown in FIG. 1b. FIG. 1c is a graph created by calculating a photocrosslinking rate at each light irradiation time when the light irradiation time is changed from 0 to 15 seconds. The horizontal axis of FIG. 1c shows the light irradiation time [sec], and the vertical axis shows the crosslinking rate [%].

[Study for Photocrosslinkable Light Wavelength]

A photocrosslinkable wavelength of the photoresponsive artificial nucleoside analog molecule (photocrosslinking element having a pyranocarbazole structure) (PyranoCarbazole Photo-Cross-Linker) ($^{PC}$X) was studied as follows:

A 50 mM sodium cacodylate buffer containing 10 µM of ODN (X), 10 µM of cODN, and 100 mM of NaCl was annealed and then irradiated with light at 4° C., and analyzed by UPLC. FIG. 2a is an explanatory diagram showing the flow of the photocrosslinking reaction. FIG. 2b summarizes the results.

[Result]

FIG. 2b is a chart for UPLC analysis when the irradiation light wavelength is changed from 450 to 550 nm. The horizontal axis in FIG. 2b is a retention time [minutes]. The positions of the peaks of the complementary strand ODN (cODN), the modified ODN (ODN ($^{PC}$X)), and the photocrosslinked ODN (*) are shown in FIG. 2b. Thus, it was found that photocrosslinking was possible by irradiation with light having a wavelength up to at least 550 nm starting from 450 nm.

[Study for Photocleavable Light Wavelength]

A photocleavable wavelength was studied for a photocrosslinked product of the photoresponsive artificial nucleoside analog molecule ($^{PC}$X).

10 µM of the photocrosslinked product was irradiated with light having 320 nm, 330 nm and 340 nm at 37° C. The same analysis was then performed. FIG. 3a is an explanatory diagram showing the flow of the photocleavage reaction. FIGS. 3b and 3c collectively show the results.

FIG. 3b is a chart for UPLC analysis when the irradiating light wavelength is changed from 320 to 340 nm. The horizontal axis in FIG. 3b is a retention time [minutes]. The positions of the peaks of the complementary ODN (cODN) and the modified ODN (ODN ($^{PC}$X)) are shown in FIG. 3b. The peak of the photocrosslinked ODN is located between 4.5 and 5 minutes of the retention time. FIG. 3c is a graph showing a ratio (a photocleavage rate % or conversion rate %) of the photocrosslinked products cleaved by irradiation with light having each wavelength. It was thus found that photocleavage was possible by irradiation with light having a wavelength of from at least 320 to 340 nm, and that within this range, irradiation with light having 330 nm had the highest photocleavage rate.

[Study for Effect of Irradiation Light Wavelength on Cells]

The following experiment was conducted in order to study that light irradiation at a longer wavelength is caused less damage to cells than light irradiation at a shorter wavelength.

100 µL of 5×10$^5$ cells/ml of cells (GFP-HeLa cells, human cervical cancer-derived strain) was dispensed into a 96-well plate and cultured in a CO$_2$ incubator for 48 hours. Subsequently, light irradiation was carried out using light having a wavelength of 366 nm, 400 nm, or 450 nm, and 10 µL of cell counting kit was then added to each well and colored in the CO$_2$ incubator for 4 hours. An absorbance at 450 nm was then measured using a microplate reader to calculate cell viability. The results are summarized in FIG. 4.

[Result]

FIG. 4 is a graph comparing the light irradiation time (seconds) with the cell viability (%) at each wavelength. This result demonstrates that the cell viability is greatly reduced by light irradiation at 366 nm even for several seconds, whereas the cell viability is not almost reduced at 400 nm and 450 nm, even if light irradiation is carried out for several tens of seconds. That is, this also reveals that pyranocarbazole can be manipulated by long-wavelength light with less cytotoxicity.

[Synthesis of Nucleoside Analog (Photoreactive Element) ($^{SPC}$X)]

As a photoresponsive artificial nucleoside analog molecule, a pyranocarbazole derivative (SPCX) having the following structure was synthesized according to Scheme 2.

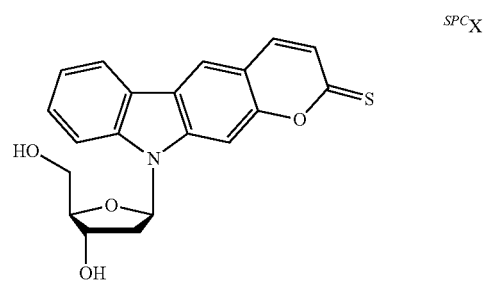

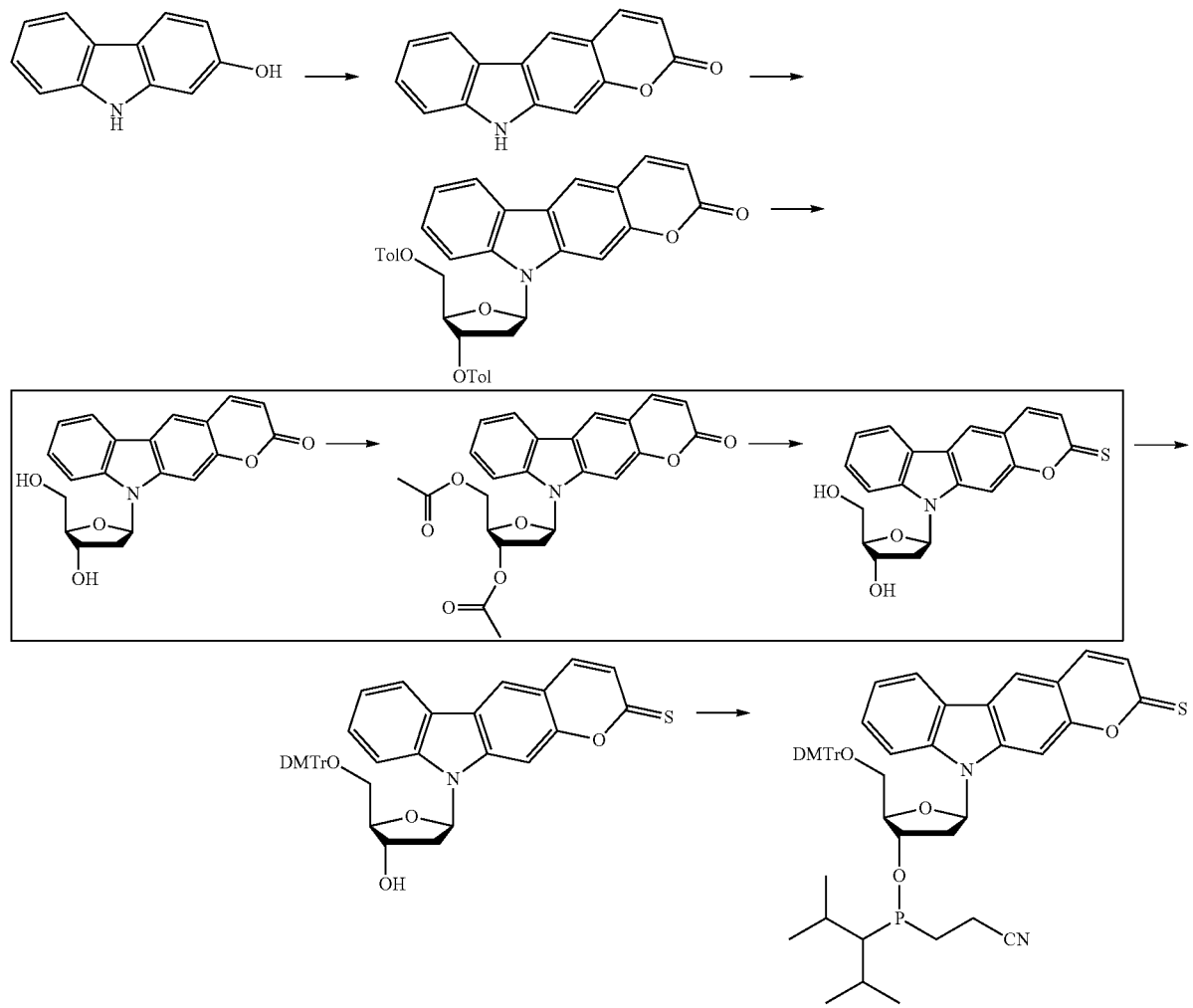

[Scheme 2]

The synthesis was carried out using 2-hydroxycarbazole as a starting material, as shown in Scheme 2, as with Scheme 1 described above. In Scheme 2, the synthesis was carried out by the same procedure as that of Scheme 1, except for the points described inside the frames. The points described inside the frames will be described below in more detail.

[Synthesis of Pyranocarbazole Derivative (S-Pyrano)]

The synthesis inside the frames in Scheme 2 was carried out as follows.

The following reaction was carried out as described below:

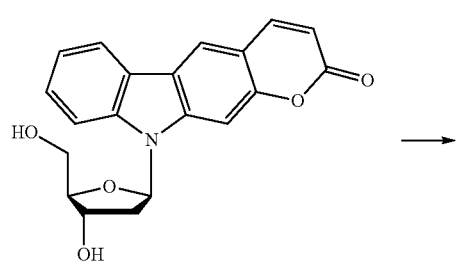

-continued

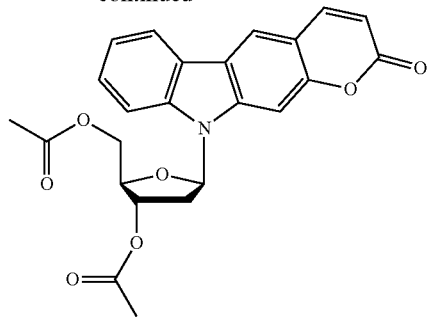

Pyranocarbazole nucleoside (800 mg, 2.28 mmol), acetic anhydride (20 mL), and DMAP (50 mg) were added to a 50 mL eggplant flask, and the mixture was stirred at room temperature for 2 hours. After confirming the progress of the reaction by TLC (CHCl$_3$:MeOH=9:1), the solvent was then removed by an evaporator, and column purification was then carried out by TLC (CHCl$_3$:MeOH=9:1). A yellow viscous liquid (7.99 mg, 1.77 mmol, 78%) was obtained. The product was identified as the target product by $^1$H-NMR.

¹H-NMR (400 MHz, CDCl₃) ∂ 8.50 (s, 1H), 8.21 (s, 1H), 8.19 (d, 1H), 7.90 (s, 1H), 7.93 (d, 1H), 7.50 (t, 1H), 7.31 (t, 1H), 6.70 (t, 1H), 6.34 (d, 1H), 5.41 (d, 1H), 5.16 (t, 1H), 4.50 (d, 1H), 3.78 (q, 2H), 2.60-2.68 (m, 1H), 2.14-2.18 (m, 1H), 1.18 (s, 6H).

The following reaction was carried out as described below:

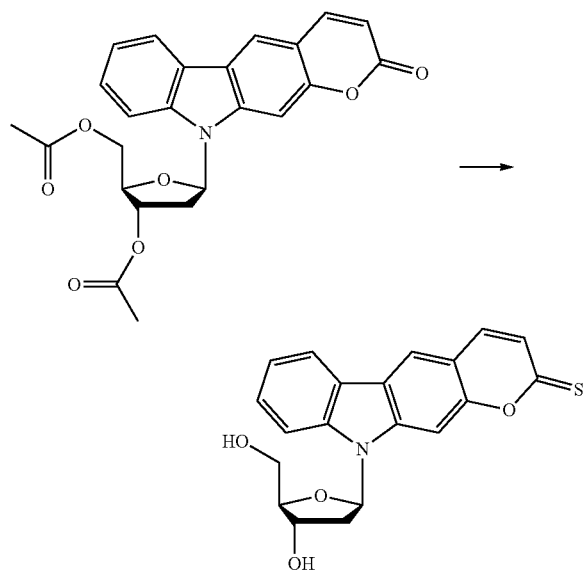

To a 50 mL eggplant flask were added 3,5-acetylpyranocarbazole nucleoside (7.99 mg, 1.77 mmol) and a Lawesson's reagent (1.00 g, 2.48 mmol), and the mixture was purged with nitrogen and stirred for 3 hours at 100° C. The appearance of a new spot was confirmed by TLC (CHCl₃:MeOH=9:1), and the reaction was stopped. The mixture was then dissolved in AcOEt, and liquid separation was then performed with an aqueous NaCl solution, the organic phase was recovered, and the solvent was removed with an evaporator. An aqueous ammonia solution was then added, and the mixture was stirred at room temperature for 60 hours. Subsequently, the ammonia was removed and water was removed by freeze-drying, and a target product was then recovered by column purification (CHCl₃:MeOH=9:1). The target product was identified by ¹H-NMR.

¹H-NMR (400 MHz, CDCl₃) ∂ 8.56 (s, 1H), 8.23 (s, 1H), 8.20 (d, 1H), 7.90 (s, 1H), 7.36 (d, 1H), 7.51 (t, 1H), 7.35 (t, 1H), 6.72 (t, 1H), 6.21 (d, 1H), 5.41 (d, 1H), 5.16 (t, 1H), 4.51 (d, 1H), 3.90 (q, 1H), 3.90 (q, 2H), 2.48-2.65 (m, 1H), 2.12-2.16 (m, 1H).

[Photocrosslinking Test with $^{SPC}$X]

Using the modified nucleic acid synthesizing monomer obtained according to Scheme 2, synthesis of a photoresponsive nucleic acid-containing DNA was carried out, confirming that it was subjected to photocrosslinking reaction.

The experiment was carried out as described below using the following ODN ($^{SPC}$X) and cODN:

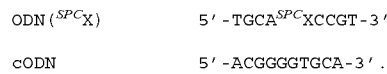

10 μM of ODN ($^{SPC}$X) and 10 μM of cODN were dissolved in a 50 mM cacodylic acid buffer (pH 7.4) containing 100 mM of NaCl, and then heated at 90° C. for 1 minute, and then cooled at 4° C. Irradiation with light having 450 nm (LED) was carried out at 4° C. Analysis was then carried out by UPLC. The analysis conditions for UPLC are as follows. The measurement was carried out at a measurement wavelength of 260 nm and at a flow rate of 0.2 mL/min, using a mixed solution of ammonium formate and acetonitrile in which the initial conditions were 99% of ammonium formate and 15% of acetonitrile, and 85% of ammonium formate and 15% of acetonitrile at the end of the analysis (10 minutes).

FIG. 5 is an explanatory diagram showing the flow of the photocrosslinking reaction.

[Result]

FIG. 6 shows the results of UPLC analysis in the photocrosslinking test. As a result of analysis by UPLC, the peaks of cODN and ODN ($^{SPC}$X), which could be confirmed before irradiation with light, were decreased depending on the light irradiation time, a new peak was confirmed, and the progress of the photocrosslinking reaction was confirmed. S-Pyranocarbazole ($^{SPC}$X) had higher photoreactivity than that of pyranocarbazole ($^{PC}$X) because the former was photocrosslinked by irradiation with light having 450 nm for 10 seconds.

INDUSTRIAL APPLICABILITY

The present invention provides a novel compound serving as a photoreactive crosslinking agent that can be used in nucleic acid photoreaction techniques. The present invention is industrially useful.

What is claimed is:

1. A compound represented by the following formula I:

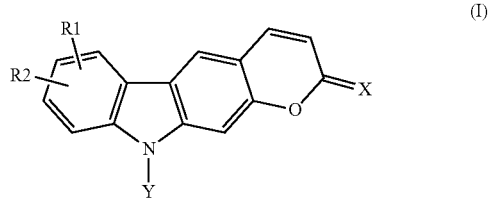

in which formula I:
X is an oxygen atom or a sulfur atom,
R1 and R2 are each independently a group selected from the group consisting of a hydrogen atom, a halogen atom, a —OH group, an amino group, a nitro group, a methyl group, a methyl fluoride group, an ethyl group, an ethyl fluoride group, and a C1-C3 alkylsulfanyl group;
Y represents a saccharide; a polysaccharide; a polyether; a polyol; a polypeptide chain; or a water-soluble synthetic polymer.

2. The compound according to claim 1, wherein Y is a group represented by the following formula II:

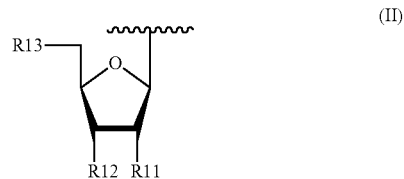

in which formula II,
R11 is a hydrogen atom or a hydroxyl group,
R12 is a hydroxyl group or a —O-$Q_1$ group,
R13 is a hydroxyl group or an —O-$Q_2$ group,
$Q_1$ is a group selected from the group consisting of:
  a phosphate group formed together with O bonded to $Q_1$;
  a nucleotide, nucleic acid or peptide nucleic acid linked via a phosphodiester bond formed by a phosphate group formed together with O bonded to $Q_1$; and
  a protecting group selected from:
    a trityl group, a monomethoxytrityl group, a dimethoxytrityl group, a trimethoxytrityl group, a trimethylsilyl group, a triethylsilyl group, a t-butyldimethylsilyl group, an acetyl group, and a benzoyl group;
$Q_2$ is a group selected from the group consisting of:
  a phosphate group formed together with O bonded to $Q_2$;
  a nucleotide, nucleic acid or peptide nucleic acid linked via a phosphodiester bond formed by a phosphate group formed together with O bonded to $Q_2$; and
  a protecting group selected from:
    a 2-cyanoethyl-N,N-dialkyl(C1-C4)phosphoramidite group, a methylphosphonamidite group, an ethylphosphonamidite group, an oxazaphospholidine group, a thiophosphite group, a TEA salt of —PH(=O)OH, a DBU salt of —PH(=O)OH, a TEA salt of —PH(=S)OH, and a DBU salt of —PH(=S)OH.

3. The compound according to claim 1, wherein Y is a group represented by the following formula III, or a group represented by the formula IV:

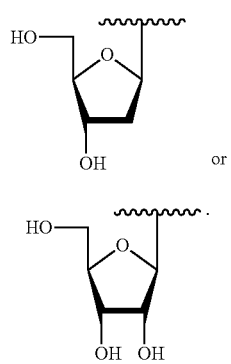

(III)

or

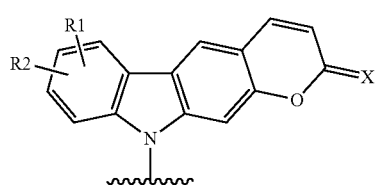

(IV)

4. The compound according to claim 1, wherein the compound is a nucleoside having, as a base moiety, a group represented by the following formula Ib:

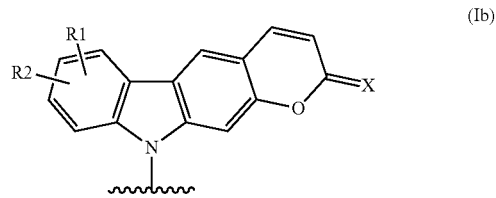

(Ib)

in which formula Ib,
X is an oxygen atom or a sulfur atom,
R1 and R2 are each independently a group selected from the group consisting of a hydrogen atom, a halogen atom, a —OH group, an amino group, a nitro group, a methyl group, a methyl fluoride group, an ethyl group, an ethyl fluoride group, and a C1-C3 alkylsulfanyl group.

5. The compound according to claim 1, wherein the compound is a nucleotide having, as a base moiety, a group represented by the following formula Ib:

(Ib)

in which formula Ib,
X is an oxygen atom or a sulfur atom,
R1 and R2 are each independently a group selected from the group consisting of a hydrogen atom, a halogen atom, a —OH group, an amino group, a nitro group, a methyl group, a methyl fluoride group, an ethyl group, an ethyl fluoride group, and a C1-C3 alkylsulfanyl group.

6. The compound according to claim 1, wherein the compound is a nucleic acid or a peptide nucleic acid having, as a base moiety, a group represented by the following formula Ib:

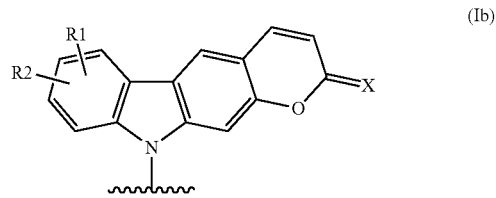

(Ib)

in which formula Ib,
X is an oxygen atom or a sulfur atom,
R1 and R2 are each independently a group selected from the group consisting of a hydrogen atom, a halogen atom, a —OH group, an amino group, a nitro group, a methyl group, a methyl fluoride group, an ethyl group, an ethyl fluoride group, and a C1-C3 alkylsulfanyl group.

7. The compound according to claim 1, wherein Y represents a saccharide.

8. The compound according to claim 7, wherein the saccharide is selected from the group consisting of ribose and deoxyribose.

9. The compound according to claim 1, wherein Y represents a polysaccharide.

10. The compound according to claim 9, wherein the polysaccharide is selected from the group consisting of a polyribose chain of a nucleic acid and a polydeoxyribose chain of a nucleic acid.

11. The compound according to claim 1, wherein Y represents a polypeptide chain.

12. The compound according to claim 11, wherein the polypeptide chain is a peptide nucleic acid.

13. A photoreactive crosslinking agent comprising the compound according to claim 1.

14. A method for forming a photocrosslink between two single-stranded nucleic acids, comprising:

hybridizing a first single-stranded nucleic acid and a second single-stranded nucleic acid, the second single-stranded nucleic acid having at least one nucleic acid base replaced by a photoreactive crosslinking agent comprising the compound according to claim 1, and irradiating the first single-stranded nucleic acid and the second single-stranded nucleic acid with light, thereby forming a crosslink between the photoreactive crosslinking agent in the second single-stranded nucleic acid and a nucleic acid base having a pyrimidine ring in the first single-stranded nucleic acid.

\* \* \* \* \*